– | United States Patent [19] | [11] Patent Number: 4,859,458
Salamone et al. | [45] Date of Patent: Aug. 22, 1989

[54] HAIR CONDITIONING POLYMERS CONTAINING ALKOXYLATED NITROGEN SALTS OF SULFONIC ACID

[75] Inventors: Ann B. Salamone, Marblehead; Susan L. Snyder, Beverly, both of Mass.

[73] Assignee: Morton Thiokol, Inc., Chicago, Ill.

[21] Appl. No.: 173,519

[22] Filed: Mar. 25, 1988

Related U.S. Application Data

[63] Continuation of Ser. No. 302,329, Sep. 15, 1981, abandoned.

[51] Int. Cl.$^4$ .......................... A61K 7/06; A61K 7/08; A61K 7/11; A61K 9/10
[52] U.S. Cl. ........................................ 424/70; 424/78; 424/81; 526/287; 526/310
[58] Field of Search ................... 424/70; 526/287, 310

[56] References Cited

U.S. PATENT DOCUMENTS 4,065,422 12/1977 Lundmark .............................. 424/70
4,128,631 12/1978 Lundmark .............................. 424/70

FOREIGN PATENT DOCUMENTS 864433 2/1971 Canada .................................. 424/70

*Primary Examiner*—Dale R. Ore
*Attorney, Agent, or Firm*—Gerald K. White

[57] ABSTRACT

Polymers containing alkoxylated nitrogen salts of sulfonic acid are useful for imparting good conditioning properties such as combability, feel, manageability, and curl retention to hair. The polymers may also comprise neutral, anionic, and/or cationic monomers.

46 Claims, No Drawings

HAIR CONDITIONING POLYMERS CONTAINING ALKOXYLATED NITROGEN SALTS OF SULFONIC ACID

This is a continuation of co-pending application Ser. No. 302,329 filed on Sept. 15, 1981, now abandoned.

BACKGROUND OF THE INVENTION

This invention generally pertains to a polymer useful for imparting good conditioning properties to hair. The polymer comprises an ethylenically unsaturated addition polymerizable monomer containing an alkoxylated nitrogen salt of sulfonic acid. The polymers may also include neutral, anionic and/or cationic monomers. Hair conditioning products generally are considered to function to improve such properties as fuel, wet and dry combability, luster, curl retention, as well as to minimize static flyaway, mend split ends, and decrease drying and defatting caused by cleaning products. Hair conditioners are routinely incorporated into such products as shampoos, creme rinses, hair colorants, hair straighteners, and hair curlers.

In the past, three types of compounds have been commonly incorporated into hair conditioning products. They are cationic polymers, proteins or protein derivatives, and fatty quaternary ammonium compounds. Commonly used cationic polymers include: quaternary nitrogen-containing hydroxyethyl cellulose compounds, copolymers of vinylpyrrolidone and dimethylamino ethyl methacrylate, and amino functional polydimethyl-siloxane. Hydrolyzed animal protein has been frequently used as a conditioner. Also used are natural products such as collagen and casein. Suitable quaternary ammonium compounds include such products as stearyl dimethyl ammonium chloride.

U.S. Pat. Nos. 4,065,422 and 4,128,631 are directed to personal care products which serve to impart a feeling of lubricity. These homopolymer products contain high molecular weight polymeric salts of 2-acrylamido-2-methylpropane sulfonic acid (AMPS). Such AMPS homopolymers have a molecular weight ranging from 1 to 5 million. Another high molecular weight sulfonate-containing homopolymer, marketed by National Starch and Chemical Corporation under the trademark "FLEXAN", is recommended for use in hair conditioners and setting lotions. This highly anionic additive is described as a polystyrene sulfonate, sodium salt, supplied as an aqueous solution at 30% solids. In addition, U.S. Pat. No. 3,937,802 discloses a hydrophilic polymer having at least 3 wt % sulfonate groups. Such polymer is disclosed to be useful for promoting curl retention when included in hair sprays. U.S. Pat. No. 4,210,161 discloses a creme rinse composition which is stated to provide for ease of combing, static control, body and setting properties. The product is an aqueous composition containing 0.02 to 2 wt % of an anionic polymer and 0.1 to 5 wt % of a cationic surfactant capable of forming a water insoluble product.

The polymer of the invention is believed to constitute a very significant improvement in the hair conditioning art because such polymer, when contrasted to the products mentioned above, exhibits a superior combination of hair care properties. These properties include wet and dry combability, feel and fly away control. The extent of the improvement will become more apparent during later portions of this disclosure.

SUMMARY OF THE INVENTION

The polymer of the invention has been found to impart excellent combability, feel, manageability, and curl retention to hair and to minimize static flyaway. In addition, such polymers are also useful for imparting anti-static properties to materials susceptible to the build-up of static electricity such as photographic films, plastic forms, carpeting, paper, and fabrics such as clothing. These polymers are generally classified as polyanionics; i.e. polymers which contain sulfonic acid groups neutralized with an alkoxylated nitrogen-containing compound. Such alkoxylated nitrogen-containing compound may conveniently be an ethoxylated amine or ethoxylated quaternary ammonium salt. The polymer includes at least one ethylenically unsaturated addition polymerizable monomer containing an alkoxylated nitrogen salt of sulfonic acid and may also include additional monomers that may be neutral, anionic and/or cationic.

Sulfonic acid containing polymers as described herein are neutralized with ethoxylated quaternary ammonium salt or ethoxylated amines to form the desired polymer of the invention. Neutralization may be effected to proportions between about 10 to 100 mole % to be employed in the practice of the invention. A range of about 25 to 100 mole % is preferred. Neutralization with an ethoxylated quaternary ammonium salt is generally depicted as follows:

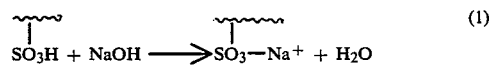
$$SO_3H + NaOH \longrightarrow SO_3^-Na^+ + H_2O \quad (1)$$

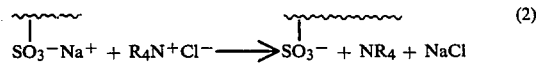
$$SO_3^-Na^+ + R_4N^+Cl^- \longrightarrow SO_3^- + NR_4 + NaCl \quad (2)$$

Neutralization with an ethoxylated amine is generally depicted as follows:

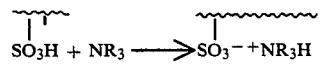
$$SO_3H + NR_3 \longrightarrow SO_3^{-+}NR_3H$$

A concentration range of from about 0.1 to 10 wt % of the polymer of the invention has been found to be useful in hair conditioning shampoos and the like. A concentration on the order of about 0.5 wt % is preferred. For other types of hair care formulations, the amount required will vary depending upon the type of treatment and quality of the hair.

Nitrogen salts of sulfonic acids include alkoxylated quaternary ammonium salts, alkoxylated amines and admixtures thereof. Quaternary ammonium salts suitable for use in the invention have the following general structure:

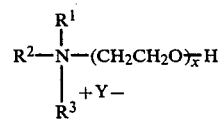

$$R^2-\underset{\underset{R^3}{|}}{\overset{\overset{R^1}{|}}{N}}-(CH_2CH_2O)_{\overline{x}}H$$
$$+Y-$$

where, $R^1$, $R^2$, $R^3$ = alkyl ($C_1$-$C_{30}$),
aryl,
$(CH_2CH_2O)_{\overline{x}}H$, or $R^1-R^2$ = cycloalkylene, -continued where, Y = halide, sulfate, and
X = 1-50

Suitable examples of alkoxylated quaternary ammonium salts include:

$$HOCH_2CH_2-\underset{\underset{coco}{+Y^-}}{\overset{\overset{CH_3}{|}}{N}}-CH_2CH_2OH$$

Methyl bis (2-hydroxyethyl) coco ammonium salt

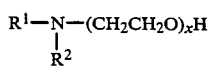

Ethyl bis (polyhydroxyethyl) alkyl ammonium salt $$CH_3(CH_2)_{17}-\underset{\underset{CH_2CH_2OH}{+Y^-}}{\overset{\overset{CH_2CH_2OH}{|}}{N}}-CH_2CH_2OH$$

Stearyl tris (2-hydroxyethyl) ammonium salt $$CH_3(CH_2)_{17}-\underset{\underset{CH_2CH_2OCH_2CH_2OH}{+Y^-}}{\overset{\overset{CH_2CH_2OCH_2CH_2OH}{|}}{N}}-CH_2CH_2OH$$

Stearyl, hydroxyethyl bis (polyhydroxyethyl) ammonium salt $$CH_3(CH_2)_{15-17}-\underset{\underset{(CH_2CH_2O)_zH}{+Y^-}}{\overset{\overset{(CH_2CH_2O)_xH}{|}}{N}}-(CH_2CH_2O)_yH$$

Cetyl, stearyl tris (polyhydroxyethyl) ammonium salt

Alkoxylated amines suitable for use in the invention have the following general structure:

$$R^1-\underset{R^2}{\overset{|}{N}}-(CH_2CH_2O)_xH$$

where, $R^1$, $R^2$, = H,
alkyl ($C_1$-$C_{30}$),
aryl,
$(CH_2CH_2O)_{\overline{x}}H$, or $R^1-R^2$ = cycloalkylene,
and
x = 1 to 50

As may be seen from the extremes of Examples 16–30, X in the above formula ranges from 7.5 to 25. This supports the following formula:

$$R^1-\underset{R^2}{\overset{|}{N}}-(CH_2CH_2O)_xH$$

where $R^1$, $R^2$ = H,
alkyl ($C_1$-$C_{30}$),
aryl
$(CH_2CH_2O)_{\overline{x}}H$, or $R^1-R^2$ = cycloalkylene
and
x = 7.5 to 25.

Suitable examples of alkoxylated amines include the following compounds:

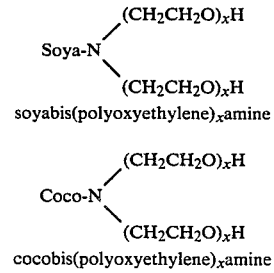

soyabis(polyoxyethylene)$_x$amine

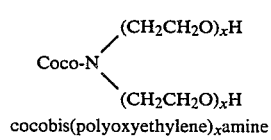

cocobis(polyoxyethylene)$_x$amine

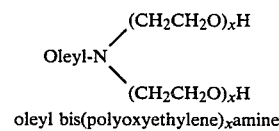

oleyl bis(polyoxyethylene)$_x$amine

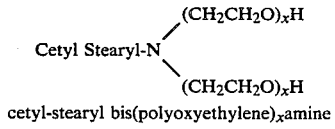

cetyl-stearyl bis(polyoxyethylene)$_x$amine

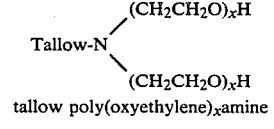

tallow poly(oxyethylene)$_x$amine

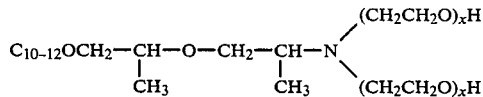

Soya bis(polyoxyethylene)$_{15}$ amine is an example of a particularly suitable ethoxylated amine salt.

Although the polymer of the invention may consist entirely of the product produced by the polymerization of ethylenically unsaturated monomer containing an alkoxylated nitrogen salt of sulfonic acid, an additional monomer may be utilized. The additional monomer (or monomers) does not add or detract from the unique properties and advantages of the sulfonic acid type polymer, but is utilized to reduce the cost of the polymer. Such polymers may be produced through vinyl polymerization monomers containing sulfonate. Such monomers include 2-acrylamido-2-methyl propane sulfonate, ethylene sulfonate, sulfoethyl methacrylate and styrene sulfonate. Structures for these monomers are shown as follows:

$$\begin{array}{c} H_2C=CH \\ | \\ C=O \\ | \\ NH \\ | \\ CH_3-C-CH_3 \\ | \\ CH_2 \\ | \\ SO_3^-X^+ \end{array}$$

2-acrylamido-2-methyl propane sulfonate $$\begin{array}{c} H_2C=CH \\ | \\ SO_3^-X^+ \end{array}$$

ethylene sulfonate $$\begin{array}{c} CH_3 \\ | \\ H_2C=C \\ | \\ C=O \\ | \\ O \\ | \\ CH_2 \\ | \\ CH_2 \\ | \\ SO_3^-X^+ \end{array}$$

sulfoethyl methacrylate

Other suitable polymers may be produced by polymer derivitization to obtain a sulfonate-containing polymer as shown below:

$$+H_2C-CH)_n\!\!\!\!\!\!\!\!\!\!\text{-}\!\phi + CH_3-\overset{O}{\underset{\|}{C}}-O-SO_3^-X^+ \longrightarrow$$

$$+H_2C-CH)_n\!\!\!\!\!\!\!\!\text{-}\!\phi\text{-}SO_3^-X^+$$

n: 2 to several million
$X^+$: alkaline earth metal such as Na, Ca, K, Li, etc: or a quaternary ammonium compound; or an ethoxylated amine such as soya bis(polyoxyethylene)$_{15}$ amine.

As stated above, the monomers containing nitrogen salts of sulfonic acid may optionally be polymerized with a second monomer. Such second monomer may be neutral, anionic, or cationic.

Suitable neutral monomers include acrylamide, substituted acrylamide, vinyl acetate, polyvinyl alcohol derived by hydrolysis of polyvinyl acetate, vinyl pyrrolidone, N-vinyl acetamide, ethylene, styrene, acrylates, methacrylates and admixtures thereof. Suitable acrylamides are set forth below:

$$\begin{array}{c} R \\ | \\ H_2C=C \\ | \\ C=O \\ | \\ N-R^2 \\ | \\ R^1 \end{array}$$

where; R = H, CH$_3$ $$R^1, R^2 = H, CH_3, CH_2OCH_3, CH_2OCH_2-\overset{CH_3}{\underset{CH_3}{\overset{|}{C}H}},$$

$(CH_2CH_2O)_{\overline{x}}H$ aryl groups, etc.

$R^1$—$R^2$ = cycloalkylene where; x = 1–50,

Acrylamides.

Suitable acrylates are set forth below:

$$\begin{array}{c} R \\ | \\ CH_2=C \\ | \\ C=O \\ | \\ O \\ | \\ R^1 \end{array}$$

where; R = H, CH$_3$
$R^1$ = alkyl groups (C$_1$ to C$_{30}$), aryl groups, $CH_2CH_2OH$, $(CH_2CH_2O)_{\overline{x}}H$, etc.

where; x = 1–50

Acrylates.

Suitable neutralized anionic monomers include acrylic acid, methacrylic acid, maleic acid, maleic acid esters, crotonic acid, vinyl phosphonate and admixtures thereof. Structures of several anionic monomers are set forth below:

$$\begin{array}{c} HC=CH \\ | \quad\quad | \\ O=C \quad C=O \\ | \quad\quad | \\ O \quad\quad O \\ | \quad\quad | \\ R \quad\quad R^1 \end{array}$$

where,
R, R$^1$ = H, alkyl groups (C$_1$ to C$_{20}$)

Maleic Acid and Esters $$\begin{array}{c} CH_3 \\ | \\ H_2C=CH \\ | \\ C=O \\ / \\ OH \end{array}$$

Crotonic Acid $$\begin{array}{c} H_2C=CH \\ | \\ C=O \\ / \\ OH \end{array}$$

Acrylic Acid $$\begin{array}{c} CH_2=CH \\ | \\ O=P=O \\ | \\ OH \end{array}$$

Vinylphosphonate

Suitable cationic monomers include vinyl amine, dimethylamino-ethyl methacrylate, vinyl pyridine, dimethyl diallyl ammonium chloride, methacrylamido propyl trimethyl ammonium chloride, vinyl benzyl trimethyl ammonium chloride, vinyl triphenyl phosphonium bromide, and admixtures thereof. Structures of several cationic monomers are set forth below:

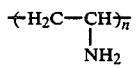

n = 2 units to several million units

Poly(vinyl amine) - (derived by hydrolysis of polyvinyl acetamide)

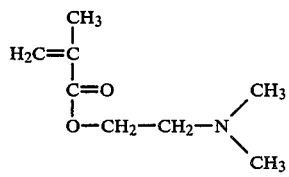

dimethyl amino ethyl methacrylate (DMAEMA)

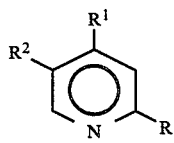

where;
R, R$^1$, R$^2$: H, CH$_2$=CH, CH$_3$

Vinyl Pyridine

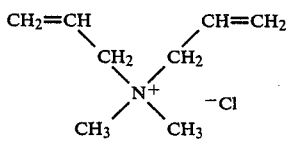

dimethyl diallyl ammonium chloride

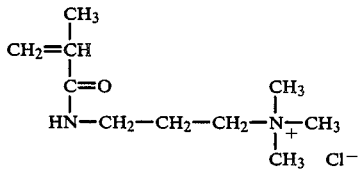

methacrylamido propyl trimethyl ammonium chloride (MAPTAC)

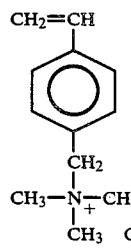

vinyl benzyl trimethyl ammonium chloride

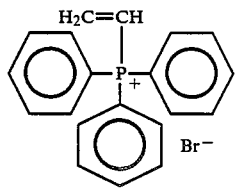

vinyl triphenyl phosphonium bromide

The polymers may be not only linear, but also may be segmental in nature. Multi-functional vinyl monomers, such as divinyl benzene or methylene bis acrylamide, may be used to promote branching of the sulfonate-containing polymers. Grafting of the sulfonate-containing monomers onto natural or synthetic polymers can be initiated by the use of ceric ammonium nitrate or benzoyl peroxide, for instance. A third approach would be to synthesize block copolymers which can be formed by the use of bifunctional initiators, e.g., di-t-butyl 4,4'-azobis(4-cyanoperoxyvalerate); or ceric ammonium nitrate-treated polyvinyl pyrrolidone (PVP) which results in triblock polymers, PVP being the center block.

The molecular weight of these polymers may be controlled by varying the amount of initiator, which could be any free radical initiator, such as ammonium persulfate, plus redox catalysts, if desired, or azobisisobutyro nitrile (AIBN); by varying the amount of chain transfer agent such as FeCl$_3$, NaHSO$_3$, mercaptan, etc.; or by varying the temperature of reaction. The polymerization itself can be achieved by solution, suspension, or emulsion techniques.

The polymers composed of alkoxylated nitrogen salts of sulfonic acid containing monomers and the additional monomer may be of various mole ratios. Suitable ratios are from about 0.03 to 1.0 of the sulfonic acid monomers with the ethoxylated amine salt being present in a mole fraction of about 0.1 to 1.0. The preferred polymer of the invention is poly(acrylamide-(co-AMPS) in a mole fraction of 9 acrylamide-1 Amps., which has been partially neutralized with soya bis(polyoxyethylene)$_{15}$ amine. Such polymer is preferred because its addition leads to superior wet combility, dry combability, feel, and anti-stat properties.

To be useful as hair conditioners, the strong acid-containing polymers should not be in the free acid form. Several salts have demonstrated usefulness, e.g., ethoxylated quaternary ammonium and ethoxylated amine salts. Neutralization (10 to 100 mole %) of sulfonic acid containing polymer with an ethoxylated nitrogen containing salt has proven especially beneficial for improving hair conditioning properties; with 40 to 60 mole % being preferred to further optimize hair conditioning properties.

The following examples and test results are believed to demonstrate the practice of the invention as well as demonstrate the superiority of the polymer when contrasted with other polymeric hair care additives.

EXAMPLE 1

A 22 liter four-neck flask fitted with reflux condenser, nitrogen purge, thermocouple, and stirrer was charged with 3,750 g (18.12 moles) of 2-acrylamido-2-methyl propane sulfonic acid (AMPS) from Lubrizol predissolved in 3,875 g of deionized water containing 0.375 g of CuSO$_4$.5H$_2$O (0.0015 m) and N$_2$ purged. In rapid succession, the following were added with stirring at room temperature: 225 g of $(NH_4)_2S_2O_8$ (0.986) predissolved in 2,250 ml of $H_2O$, 0.375 g of $FeSO_4.7H_2O$ (0.0013 m) predissolved in 125 ml of $H_2O$, and 375 g of $NaHSO_3$ (3.6 m) predissolved in 750 ml of $H_2O$, and an additional 1,125 ml of $H_2O$. After 15 minutes, polymerization began as indicated by a 25° C. exotherm (20° C. to 45° C.). After 6 hours, the reaction product was neutralized with 750 g of NaOH (18.75 m) predissolved in 750 ml of $H_2O$. The product obtained was a clear yellow liquid having a Brookfield viscosity (#3, 6 rpm) of 1,400 cp. at 35% polymer solids. Infrared spectrum confirmed the structure as poly(AMPS) with absorptions at 1650 cm$^{-1}$, 1500 cm$^{-1}$, 1220 cm$^{-1}$, 1035 cm$^{-1}$, and 615 cm$^{-1}$.

EXAMPLE 2

52.2 g of NaOH (1.3 m) was dissolved in 1,000 g of deionized $H_2O$ and 270 g of AMPS (1.3 m) was added to it, with cooling. This solution was charged to a 3-liter resin flask equipped with stirrer, condenser, thermocouple and $N_2$ purge. After purging the system with $N_2$, 5.4 g of $(NH_4)_2S_2O_8$ (0.024 m) and 0.0202 g of $FeCl_3$ (75 ppm) were added. Deionized $H_2O$ was added to bring the solids content to 15% (w/w). The solution was heated to 84±2° C. and held for 4 hours. After 1.5 hours, 6.78 g of $NaHSO_3$ (0.013 m) was added. The product obtained was a clear viscous liquid. Infrared spectrum confirmed polymer structure.

EXAMPLE 3

A 500 ml 4-neck resin kettle fitted with a thermocouple, reflux condenser, $N_2$ purge, and stirrer was charged with 18.63 g of AMPS (0.09 m) predissolved in 250 ml of deionized $H_2O$ and neutralized with 4 g of NaOH (0.1 m). While $N_2$ purging, 0.87 g of $NH_4$ lauryl sulfate (1 phm), and 0.87 g $NaH_2PO_4$ (1 phm) predissolved in 38 ml DI $H_2O$, and 0.42 g of AIBN (0.5 phm) were added. After thorough mixing, 68.8 g of vinyl acetate (0.8 m) was added and a suspension formed. The reaction temperature was maintained at 40° C. for 17 hours. A white latex was formed. The product was composed of 6 moles vinyl acetate/1 mole AMPS according to C, H, N analysis.

EXAMPLE 4

Hydrolysis of poly(vinyl acetate-(co)-AMPS (Example 3) to the free alcohol was accomplished by the addition of 3 g of 95% $H_2SO_4$ and a reaction temperature of 98° C. was maintained for 8 hours. As hydrolysis progressed, the polymer became more water soluble. The product was a white translucent viscous liquid. Infrared spectrum confirmed polymer structure.

EXAMPLE 5

A 250 ml 3-necked round bottom flask equipped with air condenser, $CaCl_2$ drying tube, and thermocouple was charged with 13.2 g of poly(AMPS-Na) (0.058 m) and 13.44 g of $PCl_5$ (0.0645 m) which were mixed as solids. The mixture was heated for 1 hour at 110° C., washed with dried diethyl ether and then dried under vacuum. The resultant light brown product was then mixed with 15.66 g of octadecyl amine (0.058 m) in a 250 ml round bottom flask and heated to 100° C. for 30 minutes. The reaction product was washed with dried diethyl ether and water. The desired polymeric product was retained in the water phase which was light amber in color. C, H, N analysis confirmed polymer structure.

EXAMPLE 6

394 g AMPS (1.9 m) was neutralized, with cooling, with 76.2 g NaOH (1.9 m) in 1125 ml deionized $H_2O$. 14.9 g acrylamide (0.21 m) was dissolved in 100 ml $H_2O$. Both monomer solutions were added to a 3-liter resin flask equiped with a reflux condenser, overhead air-driven stirrer, nitrogen inlet and thermocouple. The system was purged with $N_2$. 8 g ammonium persulfate (0.035 m) in 300 ml $H_2O$ was added. The solution was heated to 80° C. and held for 6 hours. After 1 hour, 400 ml of $H_2O$ was added. After 3 hours, 4.09 g $(NH_4)_2S_2O_8$ (0.0179 m) and 10.23 g $NaHSO_3$ (0.098 m) were added in 70 ml of $H_2O$. After 5 hours, another 4.09 g of $(NH_4)_2S_2O_8$ and 8.18 g of $NaHSO_3$ (0.078 m) in 70 ml of $H_2O$ were added. The product was a pale yellow solution. C, H, N analysis confirmed with the comonomer ratio was 9/1.

EXAMPLE 7

40 g of NaOH (1 m) was dissolved in 1,000 g of deionized $H_2O$. 207 g of 2-acrylamido-2-methylpropane sulfonic acid (1 m) was added to the NaOH solution, followed by addition of 23.7 g of acrylamide (0.33 m) in 300 g of $H_2O$. The monomers were then charged to a 3-liter resin flask equipped with an air-driven stirrer, condenser, thermocouple and $N_2$ inlet. After purging the system with $N_2$, 4.61 g of ammonium persulfate (0.02 m) in 100 g of deionized $H_2O$ was added along with 0.023 g of $FeSO_4$ (100 ppm) in 10 g of deionized $H_2O$. Additional deionized $H_2O$ was charged to the flask to bring the solids concentration to 10% (w/w). The solution was heated for 4 hours at 82±2° C. After 2 hours, 6.86 g of $NaHSO_3$ (0.065 m) and 2.74 g of $(NH_4)_2S_2O_8$ (0.012 m) were added. One hour later, 1.38 g of $NaHSO_3$ (0.013 m) was added.

EXAMPLE 8

32 g of NaOH (0.8 m) was dissolved in 1200 g of deionized $H_2O$. 165.6 g of AMPS (0.8 m) was added to the NaOH solution, with cooling. 56.8 g of acrylamide (0.8 m) was dissolved in 300 ml of deionized $H_2O$ and added to the AMPS solution. The monomers were then charged to a 3-liter resin flask equipped with an air-driven stirrer, condenser, $N_2$ inlet and thermocouple. The system was purged with $N_2$. 4.45 g of $(NH_4)_2S_2O_8$ (0.02 m) and 0.0389 g of $FeCl_3$ (175 ppm) were added to the solution, along with deionized $H_2O$ to bring the solids content to 10% (w/w). The solution was heated to 82° C. and maintained for 4 hours. After 2 hours at 82° C., 8.32 g of $NaHSO_3$ (0.08 m) was added and after 3 hours, 1.66 g of $NaHSO_3$ (0.016 m) was added.

EXAMPLE 9

14.37 g of AMPS (0.069 m) was neutralized with 2.8 g NaOH (0.069 m) predissolved in 150 ml of deionized $H_2O$. 44.0 g of acrylamide (0.63 m) was dissolved in 150 g of $H_2O$. The two monomer solutions were mixed and added to a 1-liter resin kettle equipped with reflux condenser, stirrer, $N_2$ purge, and thermocouple. After $N_2$ purging, 1.18 g of $(NH_4)_2S_2O_8$ (0.005 m) predissolved in 70 ml deionized $H_2O$ and 0.018 g of $FeCl_3$ (300 ppm) predissolved in 70 ml deionized $H_2O$ were added at room temperature. The reaction temperature was slowly raised to 80° C. and an additional 250 ml of deionized $H_2O$ added to the reaction. After 2 hours, the reaction was stopped. The product was a clear, very viscous liquid, 7.7 wt % solids.

EXAMPLE 10

82.8 g of AMPS (0.4 m) dissolved in 200 ml deionized $H_2O$ was neutralized with 16 g of NaOH (0.4 m) and charged to a 500 ml 4-neck resin kettle equipped with a stirrer, reflux condenser, thermocouple, and $N_2$ purge. To this mixture, 3.8 g of vinyl acetamide (ACE) (0.045 m) dissolved in 58 ml of $H_2O$ and 0.87 g of AIBN (0.1 phm) dispersed in 30 ml of $H_2O$ were added with stirring. The reaction mixture was $N_2$ purged and its temperature raised to 92° C. and maintained for 3 hours. Infrared spectrum and C, H, N substantiated a 9/1 comonomer ratio in the polymer.

EXAMPLE 11

After cooling, 124 g of the aqueous polymer solution of poly(AMPS-(co)-ACE) (0.013 m ACE) of Example 10 was charged into a 500 ml round bottom flask with condenser and 2.64 ml of 37% aq. HCl (0.0267 m) was added. The solution was refluxed for 20 hours. The resulting product was a pale yellow-green liquid containing 10% poly(AMPS-(co)-vinylamine) by weight. Infrared spectrum substantiates hydrolysis to the title polymer.

EXAMPLE 12

54.03 g of AMPS (0.26 m) was neutralized with 10.44 g of NaOH (0.26 m) predissolved in 240 ml of deionized $H_2O$. To a 1500 ml resin kettle fitted with the standard equipment was added the AMPS monomer solution, 200 g of vinylacetamide (2.35 m) predissolved in 340 ml of deionized $H_2O$. To a 1500 ml resin kettle fitted with the standard equipment was added the AMPS monomer solution, 200 g of vinylacetamide predissolved in 340 ml of deionized $H_2O$, and 2.54 g of azobis-isobutyronitrile (0.0132 m) predissolved in 40 ml of ethyl acetate. After $N_2$ purging, the reaction temperature was raised to 85° C. and maintained for 3 hours. The product was precipitated into acetone and dried in vacuo at 43° C. overnight. A white powder was obtained. Infrared spectrum confirmed copolymerization.

EXAMPLE 13

442.8 g of the 30% solids solution of Example 12 (1.36 m ACE) and 29.26 g of 37% HCl (2.9 m) were charged into a 1000 ml round bottom flask equipped with a reflux condenser and refluxed for 22 hours. The polymeric product was precipitated into acetone and dried in vacuo at 45° C. for 24 hours. A brown solid polymer was obtained. Infrared spectrum confirmed hydrolysis.

EXAMPLE 14

To a 500 ml resin kettle equipped with reflux condenser, stirrer, $N_2$ purge, and thermocouple was charged 20 g of AMPS (0.097 m), 13.9 g of acrylic acid (0.193 m), and 40 ml of deionized $H_2O$. To this mixture was added 1.02 g of $(NH_4)_2S_2O_8$ (0.0045 m) predissolved in 10 ml of $H_2O$, 0.003 g of $FeSO_4.7H_2O$ ($2.2\times10^{-6}$ m) predissolved in 15 ml of $H_2O$. The reactants were $N_2$ purged for 5 minutes with stirring. After 15 minutes at room temperature (22° C.), the reaction exothermed to a maximum temperature of 41° C. After 2 hours, the reaction was terminated leaving a clear viscous polymer solution of 30% solids. Infrared spectrum and percent conversion data confirmed a 2/1 mole comonomer ratio in the resultant polymer.

EXAMPLE 15

A 2-liter resin kettle was fitted with a paddle stirrer, condenser, $N_2$ inlet and 100 ml dropping funnel. 83 g of PVP K-90 (0.75 m) from GAF (nominal mol. wt. 360,000) was dissolved in one liter of distilled water. 52 g of AMPS monomer (0.25 m) was added to this solution, stirred to dissolve and transferred to the resin kettle. The contents were then purged with $N_2$ and gently stirred for 45 minutes.

The ceric ion catalyst solution was prepared by dissolving 0.140 g of ceric ammonium nitrate in 100 ml of deionized $H_2O$ containing 2.5 ml of one normal nitric acid. This catalyst was transferred to a dropping funnel and then added, by drops, to the reaction solution at 23° C. over a one hour period. After stirring overnight, the viscous solution was added to a ten-fold excess of acetone and a white-rubbery solid was precipitated. The precipitate was broken up into small pieces, washed with acetone and dried overnight at 60° C. in vacuum. The resulting solids were crushed by hand to a fine powder, washed with acetone, isolated by filtration and dried in vacuo at 56° C. overnight to afford 113 g of PVP-b-AMPS triblock polymer (84% conversion). The molecular weights of the AMPS end blocks and the PVP center block were calculated according to the procedure described in U.S. Pat. No. 3,993,712 and found to be $1\times10^5$ and $3.6\times10^5$, respectively.

EXAMPLE 16

Six individual molecular weights of polymers containing ethoxylated amine salts of sulfonic acid were synthesized by varying initiator and chain transfer agent concentrations. The procedure was as follows:

16A. A one liter resin kettle with overhead stirrer, $N_2$ inlet, condenser, thermocouple, heating mantel, and provision for external cooling was set up in a hood.

24.5 g of AMPS (0.118 m) was dissolved in 118 ml of 1N NaOH and the pH adjusted to 8, the total weight was 159.3 g. This solution was then added to the kettle along with 152.8 g of 49.4%. Dow aqueous acrylamide (1.06 m) and 100 ml of $H_2O$. Then 0.038 g of $CuCl_2.2H_2O$ dissolved in 62 ml of $H_2O$ was added. Heating, stirring, and $N_2$ purging was performed.

After about 40 minutes when after reaching a temperature of 50° C., the heating mantle was removed and 0.50 g of $(NH_4)_2S_2O_8$ dissolved in 25 ml of $H_2O$ was added, the temperature fell to 46°–47° C. Within 5 minutes the exotherm started, the solution became thicker, and the $N_2$ flow was reduced and removed to the head space. The calculated heat of polymerization at room temperature was 22.5° C., based on a 25% aqueous acrylamide solution. External cooling was applied to maintain the temperature at or below 60° C. After completion of the exotherm, a temperature of 50° C. was maintained. A sample was removed after 2 hours for acrylamide analysis, the nitrogen turned off, and 0.63 g of $NaHSO_3$ (0.5 mole % based on acrylamide) dissolved in 25 ml of $H_2O$ was added. After stirring for an hour, vacuum was pulled for 1–3 minutes several times over about a 15 minute period to help remove excess $SO_2$. While stirring vigorously, 118 g (0.059 m) of soyabis (polyoxyethylene)$_{15}$ amine was added with 75 ml of wash $H_2O$ over about 15 minutes period. After the additions, the pH was 8. Citric acid solution (25 g) was added to lower the pH to 6±0.5. The intrinsic viscosity of the polymer-sodium salt was 1.04 dl/g measured in 5.05N NaCl at 29° C.

The following additional materials were also prepared by the above described procedure. All intrinsic viscosities were measured on the sodium salt form of the polymer.

EXAMPLE NO.

Examples 16B, C, D, E and F had intrinsic viscosities of 0.875 dl/g, 1.22 dl/g, 2.15 dl/g, 7.1 dl/g and 8.55 dl/g, respectively. The final product of Examples 16 B, C, D, E and F was the soya bis(polyethylene)$_{15}$ amine salt as specified in Example 16A.

EXAMPLE 17

This Example was prepared by the method of Example 16 except that 236 g (0.118 m) of soya bis (polyoxyethylene)$_{15}$ amine was added instead of 118 g.

EXAMPLE 18

This Example was prepared by the method of Example 16 except that 55.17 g (0.059 m) of cetyl-stearyl bis (polyoxyethylene)$_{7.5}$ amine was added instead of 118 g of soya bis (polyoxyethylene)$_{15}$ amine.

EXAMPLE 19

This Example was prepared by the method of Example 16 except that 145.73 g (0.059 m) of cetyl-stearyl bis (polyoxyethylene)$_{25}$ amine was added instead of 118 g of soya bis (polyoxyethlene)$_{15}$ amine.

EXAMPLE 20

This Example was prepared by the method of Example 16 except that 291.46 g (0.118 m) of cetyl-stearyl bis (polyoxyethylene)$_{25}$ amine was added instead of 118 g of soya bis (polyoxyethylene)$_{15}$ amine.

EXAMPLE 21

This Example was prepared by the method of Example 16 except that 55.17 g (0.059 m) of tallow bis (polyoxyethylene)$_{7.5}$ amine was added instead of 118 g of soya bis (polyoxyethylene)$_{15}$ amine.

EXAMPLE 22

This Example was prepared by the method of Example 16 except that 110.33 g (0.118 m) of tallow bis(-polyoxyethylene)$_{7.5}$ amine was added instead of 118 g soya bis(polyoxyethylene)$_{15}$ amine.

EXAMPLE 23

This Example was prepared by the method of Example 16 except that 54.87 g (0.059 m) of stearyl bis(-polyoxyethylene)$_{7.5}$ amine was added instead of 118 g soya bis(polyoxyethylene)$_{15}$ amine.

EXAMPLE 24

This Example was prepared by the method of Example 16 except that 145.73 g (0.059 m) of stearyl bis(-polyoxyethylene)$_{25}$ amine was added instead of 118 g soya bis(polyoxyethylene)$_{15}$ amine.

EXAMPLE 25

This Example was prepared by the method of Example 16 except that 291.46 g (0.118 m) of steary bis(-polyoxyethylene)$_{25}$ amine was added instead of 118 g of soya bis(polyoxyethylene)$_{15}$ amine.

EXAMPLE 26

This Example was prepared by the method of Example 16 except that 52.22 g (0.059 m) of coco bis(polyoxyethylene)$_{7.5}$ amine was added instead of 118 g of soya bis(polyoxyethylene)$_{15}$ amine.

EXAMPLE 27

This Example was prepared by the method of Example 16 except that 73.46 g (0.059 m) of an ethoxylated amine having the structure shown below was added instead of 118 g of soya bis (polyoxyethylene)$_{15}$ amine.

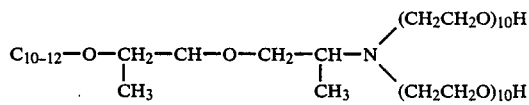

EXAMPLE 28

This Example was prepared by the method of Example 16 except that 146.92 g (0.18 m) of an ethoxylated amine having the structure shown below was added instead of 118 g of soya bis (polyoxyethylene)$_{15}$ amine.

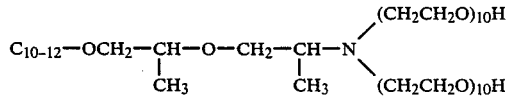

EXAMPLE 29

20 g of a poly(2-acrylamido-2-methyl propane sodium sulfonate) 0.09 m) (Example 1) dissolved in 37 g of water was adjusted to pH 4.0 with citric acid. 66 g soya bis(polyoxyethylene)$_{15}$ amine (0.045 m) was then reacted and the pH adjusted to 6.5.

EXAMPLE 30

20 g of a solution of 35% by weight 2-acrylamido 2-methyl propane sodium sulfonate (0.03 m) (Example 1) adjusted to pH 6 with NaOH, was reacted while mixing with 15.3 g of methyl polyoxyethylene$_{(15)}$ octadecylammonium chlorde (0.015 m).

Each of the neutralized sulfonic acid-containing polymers prepared in the above Examples was evaluated as a hair conditioner. Specifically, each polymer was evaluated with respect to the following properties: wet/dry combing, feel, curl retention, and static fly away. All polymers were evaluated in a model conditioner and shampoo/conditioner formulation. The test procedures are set forth below and the respective results are recorded in Tables I-V.

Each polymer as well as a selection of commercial additives were evaluated sequentially for wet and dry combability and feel in model conditioner and shampoo/conditioner. Performance was evaluated by independent observers on coded samples using a rating of 1 to 10 (poor to excellent).

A separate 2 gram swatch was used for each product. The 8" dark brown virgin hair was obtained from DeMeo Bros., 39 W. 28th St., New York, N.Y. 10001. The swatch was immersed in the model formulation solution for 1 minute, rinsed with running tap water for 5 seconds, and dunked 10 times in distilled water. The swatch was subsequently evaluated as follows:

Combability—Wet:
  The swatch was combed wet and rated for ease of combing.

Combability—Dry:
After wet combing, the swatch was air dried, combined and rated again for ease of combining.

Feel:
After dry combing, each swatch was evaluated for feel by two (2) people and rated.

The above test sequence was repeated four (4) times on the swatch for each material tested. The results shown in Tables I and II are expressed as an average of these ratings.

Examples 16 through 25 were evaluated using a rating of 1 to 10 for dry combability and feel; however, wet combability was assessed in a different manner from the previous examples (1–15). The time in seconds were recorded in which it took to completely detangle each wet swatch; the less the time, the better the detangling ability of the conditioner. In order to record a meaningful detangling time, 3 of 18" dark brown virgin hair was used for each swatch. The results shown in Tables III and IV are given as an average of wet comb times expressed in seconds. Dry combability and feel are expressed as ratings (1–10) for two swatches tested 4 times each.

Following completion of the comb and feel tests, the hair swatches were evaluated for curl retention as follows:

The dry swatch was dipped in water, curled wet on ½-inch diameter rollers and air dried. It was then placed in a humidity chamber set at 85% RH, 72° F. The curler was removed upon placement in the chamber. After 1 hour exposure, the length of the hair swatch was measured and curl retention calculated using the equation below.

Additionally, each product was tested as a setting gel. Upon completion of the above curl retention test, each dry swatch was dipped into the conditioning formulation for 90 seconds, curled on a ½-inch roller and air dried. It was then placed in the aforementioned humidity chamber. After 1 hour exposure, the hair swatch length was measured. The percent curl retention was calculated using the equation below (Table V).

$$\% \text{ Curl Retention} = \frac{\text{(Initial Length} - \text{Uncurled Length)}}{\text{(Initial Length} - \text{Curled Length)}} \times 100$$

It should be mentioned that all test methods are subject to human appraisal and thus should be considered to give subjective results although every effort was made to insure unbiased opinions. The data are qualitative rather than quantitative.

Examples 1–15 are considered to depict various Sulfonic Acid containing polymers that have not been neutralzied with an alkoxylated nitrogen containing salt and, hence, represent a basis from which to evaluate the effect of neutralization in accordance with this invention. Example 16A was made in accordance with this invention and demonstrates a clear overall superiority over alkali metal (Na) neutralized polymers with respect to the conditioning properties.

Curl retention, in some cases, was demonstrated to be at least as good as the comparative commercial products.

These results are listed in Tables I, II and V. Tables III and IV contain additional test data for polymers of the invention. It is also pointed out that the polymer of the invention has been contrasted with seven commercially available polymers. As in the comparison with the alkali metal neutralized polymers, the polymer of the invention possesses a clear general superiority in relevant hair care properties. The commercially available polymers are discussed further in Table VI.

TABLE I

| Material Tested | Performance in a Model Conditioner[a] | | | | |
|---|---|---|---|---|---|
| | pH | Wet Comb | Dry Comb | Feel | Fly Away Control |
| Example 1 | 6 | 6.1 | 7.9 | 6.3 | Excellent |
| Example 2 | 6 | 5.7 | 7.5 | 6.3 | Excellent |
| Example 2S[b] | 6 | 7.5 | 8.6 | 6.8 | Excellent |
| Example 3 | 11.0 | 5.8 | 8.0 | 7.0 | Good |
| Example 4 | 11.2 | 7.8 | 8.0 | 7.3 | Good |
| Example 5 | 8.6 | 7.3 | 8.0 | 4.6 | Good |
| Example 6 | 6 | 8.6 | 7.9 | 7.5 | Excellent |
| Example 7 | 6 | 8.9 | 7.9 | 6.6 | Excellent |
| Example 8 | 6 | 7.5 | 7.9 | 7.0 | Excellent |
| Example 9 | 6 | 8.2 | 7.5 | 7.0 | Excellent |
| Example 10 | 6 | 6.4 | 6.8 | 6.1 | Excellent |
| Example 11 | 7.4 | 6.5 | 8.0 | 5.6 | Good |
| Example 12 | 6 | 7.5 | 6.4 | 5.5 | Good |
| Example 13 | 6 | 4.3 | 6.1 | 4.1 | Average |
| Example 15 | 6 | 5.7 | 7.1 | 6.6 | Good |
| Example 16A | 6 | 9.0 | 8.0 | 8.0 | Excellent |
| Polymer JR | 6 | 7.1 | 7.9 | 5.7 | Poor |
| Stearylalkonium Chloride | 6 | 7.9 | 7.5 | 6.8 | Average |
| Flexan 130 | 6 | 8.5 | 8.5 | 5.1 | Excellent |
| Merquat 550 | 6 | 7.3 | 8.8 | 6.4 | Average |
| GAF 550 | 6 | 9.3 | 8.3 | 6.0 | Poor |
| PVP (K-90) | 6 | 7.3 | 9.0 | 6.0 | Poor |
| Carbopol 940 | 6 | 7.3 | 8.3 | 7.0 | Good |
| Blank | 6 | 6.2 | 7.2 | 5.5 | Average |

[a]Formulation: 0.5 parts Polymer or Commercial additive
99.5 parts Distilled Water
pH adjusted with HCl or NaOH
[b]Stearyl benzyl dimethyl ammonium salt of poly (AMPS) from Example 2.

TABLE II

| | Performance in a Model Shampoo/Conditioner[a] | | | |
|---|---|---|---|---|
| Material Tested | pH | Wet Comb | Dry Comb | Feel |
| Example 1 | 6 | 6.8 | 6.8 | 7.3 |
| Example 2 | 6 | 6.8 | 7.9 | 7.3 |
| Example 2S | 6 | 7.5 | 7.9 | 7.7 |
| Example 3 | 7.5 | 5.0 | 8.0 | 5.3 |
| Example 4 | 9.0 | 8.0 | 8.0 | 5.3 |

TABLE II-continued

Performance in a Model Shampoo/Conditioner[a]

| Material Tested | pH | Wet Comb | Dry Comb | Feel |
|---|---|---|---|---|
| Example 5 | 8.5 | 5.0 | 8.0 | 6.5 |
| Example 6 | 6 | 6.1 | 7.1 | 7.9 |
| Example 7 | 6 | 6.1 | 7.5 | 7.5 |
| Example 8 | 6 | 5.7 | 7.9 | 6.8 |
| Example 9 | 6 | 9.3 | 8.6 | 7.3 |
| Example 10 | 6 | 5.7 | 7.9 | 8.0 |
| Example 11 | 7.4 | 7.3 | 8.0 | 6.4 |
| Example 12 | 6 | 7.5 | 7.5 | 7.9 |
| Example 13 | 6 | 6.4 | 8.2 | 6.6 |
| Example 14 | 8.5 | 4.5 | 8.0 | 6.5 |
| Example 15 | 6 | 5.4 | 7.1 | 7.7 |
| Example 16 A[b] | 6 | 8.5 | 8.7 | 8.0 |
| Polymer JR | 6 | 8.9 | 8.6 | 7.3 |
| Stearylalkonium Chloride | 6 | 5.4 | 7.1 | 7.5 |
| Flexan 130 | 6 | 6.3 | 8.5 | 7.8 |
| Merquat 550 | 6 | 8.5 | 9.0 | 8.3 |
| GAF 755N | 6 | 5.3 | 8.8 | 7.4 |
| PVP (K-90) | 6 | 7.0 | 8.8 | 7.4 |
| Carbopol 940 | 6 | 5.8 | 8.8 | 8.1 |
| Blank | 6 | 6.2 | 6.2 | 6.4 |

[a]Formulation: 0.5 parts Polymer or Commercial Additive, 12.5 parts Ammonium Lauryl Sulfate, 87.0 parts Distilled Water, pH adjusted with HCl or NaOH
[b]Hair tested was 18 inch, dark brown virgin hair.

TABLE III

Performance of Ethoxylated Polymers in Model Conditioner[a]

| Material Tested | Wet Comb (sec.) | Dry Comb (1-10) | Feel (1-10) |
|---|---|---|---|
| Example 16A | 9.1 | 9.3 | 8.3 |
| Example 16B | 5.1 | 8.7 | 8.3 |
| Example 16C | 5.9 | 9.5 | 8.7 |
| Example 16D | 6.9 | 9.3 | 8.3 |
| Example 16E | 22.0 | 8.3 | 7.7 |
| Example 16F | 3.9 | 9.2 | 7.6 |
| Example 17 | 6.2 | 9.7 | 8.3 |
| Example 18 | 8.7 | 6.9 | 7.4 |
| Example 19 | 9.7 | 8.4 | 7.9 |
| Example 20 | 8.1 | 9.3 | 8.3 |
| Example 21 | 10.5 | 9.0 | 7.3 |
| Example 22 | 7.2 | 8.7 | 7.9 |
| Example 23 | 9.5 | 7.5 | 7.3 |
| Example 24 | 18.5 | 8.3 | 8.4 |
| Example 25 | 18.3 | 8.9 | 7.7 |
| Example 26 | 8.7 | 6.1 | 7.9 |
| Example 29 | 12.7 | 9.0 | 8.2 |
| Example 30 | 10.8 | 9.3 | 7.9 |
| Blank | 16.5 | 7.9 | 7.7 |

[a]Formulation: 0.5 parts polymer
99.5 parts distilled water
pH adjusted to 6.0 ± .2 with citric acid or NaOH

TABLE IV

Performance of Ethoxylated Polymers in Model Conditioning Shampoo[a]

| Material Tested | Wet Comb (sec.) | Dry Comb (1-10) | Feel (1-10) |
|---|---|---|---|
| Example 16A | 22.4 | 8.7 | 8.0 |
| Example 16B | 35.9 | 8.1 | 7.6 |
| Example 16C | 22.5 | 9.2 | 8.7 |
| Example 16D | 22.4 | 8.7 | 8.0 |
| Example 16E | 28.4 | 8.7 | 7.8 |
| Example 16F | 36.8 | 8.2 | 7.7 |
| Example 17 | 29.5 | 8.7 | 7.9 |
| Example 18 | 38.1 | 6.3 | 7.9 |
| Example 19 | 48.8 | 8.4 | 7.7 |
| Example 20 | 37.8 | 8.8 | 8.3 |
| Example 21 | 41.9 | 8.2 | 7.7 |
| Example 22 | 34.8 | 8.4 | 7.6 |
| Example 23 | 48.6 | 6.3 | 7.7 |
| Example 24 | 54.3 | 7.9 | 7.8 |
| Example 25 | 29.3 | 7.6 | 7.7 |
| Example 26 | 49.4 | 6.5 | 7.5 |
| Example 27 | 39.5 | 8.75 | 8.4 |
| Example 28 | 30.8 | 7.8 | 8.3 |
| Example 29 | 49.2 | 7.5 | 7.9 |
| Example 30 | 51.7 | 7.9 | 7.4 |
| Blank | 51.6 | 7.3 | 7.5 |

[a]Formulation: 0.5 parts polymer
12.5 parts ammonium lauryl sulfate
87 parts distilled water
pH adjusted to 6 ± 0.2 with citric acid or NaOH

TABLE V

| | Curl Retention | | |
|---|---|---|---|
| Material Tested | Curl Retention on Model[b] Shampoo/Conditioner | Curl Retention[a] In Conditioner | Curl Retention[a] In Setting Gel |
| Example 1 | 7.7% | 7.7% | 11.5% |
| Example 2 | 15.4% | 15.4% | 26.9% |
| Example 2S | 19.2% | 11.5% | 11.5% |
| Example 3 | 29.0% | 18.0% | — |
| Example 4 | 18.0% | 23.5% | — |
| Example 5 | 32.0% | 28.0% | — |
| Example 6 | 15.4% | 15.4% | 19.2% |
| Example 7 | 19.2% | 19.2% | 19.2% |
| Example 8 | 23.1% | 15.4% | 15.4% |
| Example 9 | 15.4% | 19.2% | 80.8% |
| Example 10 | 19.2% | 11.5% | 7.7% |
| Example 11 | 22.0% | 29.0% | — |
| Example 12 | 15.4% | 30.8% | 15.4% |
| Example 13 | 19.2% | 11.5% | 26.9% |
| Example 15 | 15.7% | 7.7% | 11.5% |
| Example 16 | 15.0% | 15.0% | — |
| Example 29 | 17.8% | 14.3% | — |
| Polymer JR | 15.4% | 26.9% | 92.3% |
| Stearylalkonium Chloride | 19.2% | 26.9% | 23.1% |
| Flexan 130 | 15.4% | 7.7% | 15.4% |
| Merquat 550 | 21.7% | 11.5% | 30.8% |
| GAF 755N | 11.5% | 19.2% | 19.2% |
| PVP (K-90) | 26.1% | 30.8% | 19.2% |
| Carbopol 940 | 11.5% | 30.8% | 88.5% |

TABLE V-continued

| Material Tested | Curl Retention on Model[b] Shampoo/Conditioner | Curl Retention[a] In Conditioner | Curl Retention[a] In Setting Gel |
|---|---|---|---|
| | Curl Retention | | |
| Blank | 19.2% | 15.4% | 15.4% |

[a]Formulation: 0.5 parts Polymer or Commercial Additive, 99.5 parts Distilled Water, pH Adjusted with HCl or NaOH
[b]Formulation: 0.5 parts Polymer or Commercial Additive, 12.5 parts Ammonium Lauryl Sulfate, 87.0 parts Distilled Water, pH Adjusted with HCl or NaOH

TABLE VI

| POLYMER | DESCRIPTION |
|---|---|
| Polymer JR | quaternary nitrogen-containing hydroxyethyl cellulose |
| Stearylalkonium Chloride | stearyl benzyl dimethyl ammonium chloride |
| Flexan 130 | sodium poly(styrene sulfonate) |
| Merquat 550 | poly(acrylamide-(co)-diallyl dimethyl ammonium chloride) |
| GAF 775N | poly(vinyl pyrrolidone-(co)-dimethyl amino ethyl methacrylate) |
| PVP (K-90) | poly(vinyl pyrrolidone) 360,000 mol. wt. |
| Carbopol 940 | lightly crosslinked poly(acrylic acid) |

We claim:

1. A polyanionic polymer for imparting good conditioning properties to hair made from an ethylenically unsaturated addition polymerizable monomer containing an alkyloxylated nitrogen salt of sulfonic acid, and at least one additional monomer selected from the group consisting of neutral monomers, anionic monomers, or cationic monomers; said addition polymerizable monomer being present in a mole fraction of about 0.03 to 1.0; said salt being derived from an ethoxylated amine having the following structure:

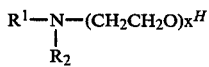

where $R^1, R^2 =$ H,
alkyl ($CH_1$—$C_{30}$),
aryl
$(CH_2CH_2O)_xH$, or
$R^1$—$R^2 =$ cycloalkylene
and $x = 7.5$ to 25;

2. The polymer of claim 1, wherein: said polymerizable monomer comprises at least one ethylenically unsaturated addition polymerizable monomer containing an ethoxylated nitrogen salt of sulfonic acid.

3. The polymer of claim 1, wherein: said additional monomer is a neutral monomer and is a member selected from the group consisting of acrylamide, substututed acrylamide, vinyl acetate, vinyl pyrrolidone, N-vinyl acetamide, ethylene, styrene, acrylate, and admixtures thereof.

4. The polymer claim 1, wherein: said second monomer is an anionic monomer and is a member selected from the group consisting of acrylic acid, maleic acid, maleic acid esters, crotonic acid, vinyl phosphonate, and admixtures thereof.

5. The polymer of claim 1, wherein: said second monomer is a cationic monomer and is a member selected from the group consisting of vinyl amine, dimethylamino-ethyl methacrylate, vinyl pyridine, dimethyl diallyl ammomium chloride, methacrylamido propyl trimethyl ammonium chloride, vinyl benzyl trimethyl ammonium chloride, vinyl triphenylphosphonium bromide, and admixtures thereof.

6. The polymer of claim 1, wherein: said polymerizable monomer comprises 2-acrylamido 2-methyl propane sulfonate.

7. The polymer of claim 6, wherein: said additional monomer comprises acrylamide.

8. The polymer of claim 7, wherein: said salt comprises soya bis(polyoxyethylene)$_{15}$ amine.

9. The polymer of claim 8, wherein: said salt is present in a mole fraction of about 0.1 to 1.0.

10. The polymer of claim 9, wherein: said salt is present in a mole fraction of about 0.4 to 0.6.

11. The polymer of claim 1, wherein: said salt comprises soy bis(polyoxyethylene)$_{15}$ amine.

12. The polymer of claim 1, wherein: said salt comprises cetyl-stearyl bis(polyoxyethylene)$_{7.5}$ amine.

13. The polymer of claim 1, wherein: said salt comprises cetyl-stearyl bis(polyoxyethylene)$_{25}$ amine.

14. The polymer of claim 1, wherein: said salt comprises tallow bis(polyoxyethylene)$_{7.5}$ amine.

15. The polymer of claim 1, wherein: said salt comprises stearyl bis(polyoxyethylene)$_{7.5}$ amine.

16. The polymer of claim 1, wherein: said salt comprises stearyl bis(polyoxyethylene)$_{25}$ amine.

17. The polymer of claim 1, wherein: said salt comprises coco bis(polyoxyethylene)$_{7.5}$ amine.

18. The polymer of claim 1, wherein: said ethoxylated amine comprises tallow poly(oxyethylene)$_x$ amine.

19. The polymer of claim 1, wherein: said ethoxylated amine has the following structure:

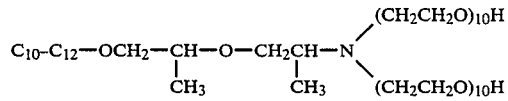

20. The polymer of claim 1, wherein: said ethoxylated amine comprises soya bis(polyoxyethylene)$_x$ amine.

21. The polymer of claim 1, wherein: said ethoxylated amine comprises coco bis(polyoxyethylene)$_x$ amine.

22. The polymer of claim 1, wherein: said ethoxylated amine comprises oleyl bis(polyoxyethylene)$_x$ amine.

23. The polymer of claim 1, wherein: said ethoxylated amine comprises cetyl-stearyl bis(polyoxyethylene)$_x$ amine.

24. The polymer of claim 1, wherein: said ethoxylated amine comprises tallow poly(oxyethylene)$_x$ amine.

25. A hair conditioning product containing the polymer of claim 10 in an amount from 0.1 to 10 wt. %.

26. A method of conditioning hair, comprising applying a composition comprising the product of claim 25 to hair so as to obtain good hair conditioning properties.

27. A polyanionic polymer for imparting good conditioning properties to hair made from an ethylenically unsaturated addition polymerizable monomer being present in a mole fraction of about 0.03 to 1.0 and containing an alkoxylated nitrogen salt of sulfonic acid; said salt being derived from an ethoxylated quaternary ammonium salt having the following structure:

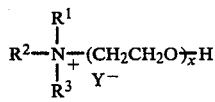

where, $R^1, R^2, R^3 =$ [H]
alkyl $(C_1-C_{30})$,
aryl,
$(CH_2CH_2O)_{\overline{x}}H$, or
$R^1-R^2 =$ cycloalkylene,
where, $Y =$ halide, sulfate, and
$X = 1-50$.

28. The polymer of claim 27, wherein: said polymer includes at least one additional monomer selected from the group consisting of neutral monomers, anionic monomers, cationic monomers, or admixtures thereof.

29. The polymer of claim 27, wherein: said polymerizable monomer comprises at least one ethylenically unsaturated addition polymerizable monomer containing an ethoxylated nitrogen salt of a sulfonic acid.

30. The polymer of claim 28, wherein: said polymerizable monomer comprises at least one ethylenically unsaturated addition polymerizable monmomer containing an ethoxylated nitrogen salt of a sulfonic acid.

31. The polymer of claim 28, wherein: said additional monomer is a neutral monomer and is a member selected from the group consisting of acrylamide, substituted acrylamide, vinyl acetate, vinyl pyrrolidone, N-vinyl acetamide, ethylene, styrene, acrylate, and admixtures thereof.

32. The polymer of claim 28, wherein: said second monomer is an anionic momomer and is a member selected from the group consisting of acrylic acid, maleic acid, maleic acid esters, crotonic acid, vinyl phosphonate and admixtures thereof.

33. The polymer of claim 28, wherein: said second monomer is a cationic monomer and is a member selected from the group consisting of vinyl amine, dimethylamino-ethyl methacrylate vinyl pyridine, dimethyl diallyl ammonium chloride, methacrylamido propyl trimethyl ammonium cloride, vinyl benzyl trimethyl ammonium chloride, vinyl triphenylphosphonium bromide, and admixtures thereof.

34. The polymer of claim 28, wherein: said polymerizable monomer comprises 2-acrylamido 2-methyl propane sulfonate.

35. The polymer of claim 34, wherein: said additional monomer comprises acrylamide.

36. A hair conditioning product containing the polymer of claim 35.

37. A method of conditioning hair, comprising applying a composition comprising the product of claim 36 to hair so as to obtain good hair conditioning properties.

38. The polymer of claim 27, wherein: said alkoxylated quaternary ammonium salt comprises methyl bis(2-hydroxyethyl) coco ammonium salt.

39. The polymer of claim 27, wherein: said alkoxylated quaternary ammonium salt comprises ethyl bis(-polyhydroxyethyl) alkyl ammonium salt.

40. The polymer of claim 27, wherein: said alkoxylated quaternary ammonium salt comprises stearyl tris(2-hydroxyethyl) ammonium salt.

41. The polymer of claim 27, wherein: said alkoxylated quaternary ammonium salt comprises stearyl, hydroxyethyl bis(polyhydroxyethyl) ammonium salt.

42. The polymer of claim 27, wherein: said alkoxylated quaternary ammonium salt comprises cetyl, stearyl tris(polyhydroxyethyl) ammonium salt.

43. A hair conditioning product being a member selected from the group consisting of shampoo, and conditioner: said product containing from 0.1 to 10 wt. % of a polyanionic polymer made from an ethylenically unsaturated addition polymerizable monomer containing an alkoxylated nitrogen salt of sulfonic acid; said addition polymerizable monomer being present in a mole fraction of about 0.3 to 1.0; said salt being derived from an ethoxylated amine having the following structure:

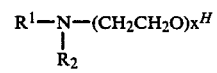

where $R^1, R^2 =$ H,
alkyl $(CH_1-C_{30})$,
aryl
$(CH_2CH_2O)_xH$, or
$R^1-R^2 =$ cycloalkylene
and $x = 7.5$ to 25;

said product having the properties of imparting excellent combability, feel, manageability, and curl retention to hair and minimizing static flyaway.

44. A method of conditioning hair, comprising applying the product of claim 43 to hair.

45. A hair conditioning product being a member selected from the group consisting of shampoo, and conditioner; said product containing from 0.1 to 10 wt. % of polyanionic polymer made from an ethylenically unsaturated addition polymerizable monomer containing an alkoxylated nitrogen salt of sulfonic acid; said addition polymerizable monomer being present in a mole fraction of about 0.03 to 1.0; said salt being derived from an ethoxylated quaternary ammonium salt having the following structure:

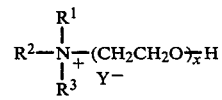

where, $R^1, R^2, R^3 =$ [H]
alkyl $(C_1-C_{30})$,
aryl,
$(CH_2CH_2O)_{\overline{x}}H$, or
$R^1-R^2 =$ cycloalkylene,
where, $Y =$ halide, sulfate, and
$X = 1-50$;

said product having the properties of imparting excellent combability, feel, manageability, and curl retention to hair and minimizing static flyaway.

46. A method of conditioning hair, comprising applying the product of claim 45 to hair.

* * * * *

UNITED STATES PATENT AND TRADEMARK OFFICE
CERTIFICATE OF CORRECTION

PATENT NO. : 4,859,458

DATED : Aug. 22, 1989

INVENTOR(S) : Ann B. Salamone and Susan L. Snyder

It is certified that error appears in the above-identified patent and that said Letters Patent is hereby corrected as shown below:

Column 1, line 17, delete "fuel" and insert --feel--.

Column 8, line 28, change "catalysts" to --catalyst--.

Column 8, line 44, change "combility" to --combability--.

Column 13, Example 25, line 63, change "steary" to --stearyl--.

Column 14, Example 28, line 19, change "0.18" TO --0.118--.

Column 15, Example 30, line 2-3, change "combined" to --combed--, and "combining" to --combing--.

Column 15, Example 30, line 14, change "were" to --was--.

Column 15, Example 30, line 18, change "3" to --3g--.

Column 21, Claim 27, line 9, delete [H].

Column 22, Claim 45, line 50, delete [H].

Signed and Sealed this

Twenty-eighth Day of July, 1992

Attest:

DOUGLAS B. COMER

Attesting Officer  Acting Commissioner of Patents and Trademarks